United States Patent [19]

Fatemi

[11] 4,138,082
[45] Feb. 6, 1979

[54] REMOTELY OPERATED, X-Y TRANSLATION SLIDE WITH STATIONARY MOTORS

[75] Inventor: Mohammad Fatemi, McLean, Va.

[73] Assignee: The United States of America as represented by the Secretary of the Navy, Washington, D.C.

[21] Appl. No.: 801,446

[22] Filed: May 27, 1977

[51] Int. Cl.² ............................................. F16M 13/00
[52] U.S. Cl. .................................... 248/419; 248/422; 269/60
[58] Field of Search ..................... 248/1, 23, 419, 422; 269/60; 356/196, 244

[56] References Cited

U.S. PATENT DOCUMENTS

| | | | |
|---|---|---|---|
| 3,124,018 | 3/1964 | Gough | 269/60 |
| 3,270,423 | 9/1966 | Birrel et al. | 269/70 X |
| 3,384,748 | 5/1968 | Rioux et al. | 269/60 X |
| 3,432,135 | 3/1969 | Carr | 248/419 X |
| 3,790,155 | 2/1974 | Longamore | 108/137 X |
| 3,801,090 | 4/1974 | Gillen | 269/60 |
| 4,013,280 | 3/1977 | Chitayat | 269/60 |

Primary Examiner—William H. Schultz
Attorney, Agent, or Firm—R. S. Sciascia; Philip Schneider

[57] ABSTRACT

Apparatus for providing remote-operated two dimensional translation in a vertical plane in an accurate and reliable manner for use in a laboratory sampling system, comprises two translation stages with a moveable slide affixed to one of such stages, mounted so as to be independently translatable in orthogonal directions in the vertical plane and are coupled to an integral drive system in such a manner so as to result in a compact unit.

1 Claim, 3 Drawing Figures

REMOTELY OPERATED, X-Y TRANSLATION SLIDE WITH STATIONARY MOTORS

BACKGROUND OF THE INVENTION

1. Field of the Invention

The present invention relates to the field of translation devices for use with laboratory sampling systems and particularly to remote-operated translation devices for providing two dimensional translation of a sampling system in a vertical plane, in a simple, accurate, independent and reliable manner.

2. Description of the Prior Art

In the past, translation stages used in remote-operated two dimensional translation slide were constructed in such a manner that the weight of the motor used to translate one stage, would be supported by the other stage. For example, where the translation slide consists of two stages, one mounted vertically over the other, the weight of the motor used to drive the upper stage would result in a load on the lower stage. As the upper stage was driven by the motor or the lower stage was driven by its motor, the distance from where the upper motor was mounted to the lower stage varied. This resulted in an additional load on the lower stage, in addition to the weight of the object being translated, that varied whenever the placement of the two stages with respect to each other changed. It was thus not possible to accurately and simply translate the object of the translation. A complex slide was calculated to correct the desired positional movement of the translation side for the variation of the load placed upon the lower stage by the motor driving the upper stage. This resulted in a long and tedious process of calculations and a longer period of activity was necessary to obtain correct positional translation of the object to the desired location. Further, any such translation table constructed could not heretofore be made as compactly as desired as a unit.

In the laboratory, it is often necessary to perform tests upon a multitude of samples, each of which may be contained in a test tube which is mounted in a circular sample disk. The disk is then rotated until each test has been performed upon each sample. It is frequently desired to provide for adjustment of the samples a small distance (typically a ½ inch) in either the X or Y direction or both, to obtain the correct relationship between the samples and the test equipment. Heretofore, the remote-operated translation slide available for this purpose were of such construction to comprise an assembly where the load the upper motor placed on the lower motor had to be constantly calculated in order to attain X-Y translation of at best a minimally acceptable accuracy.

Devices used in the manufacture of integrated circuits, such as that disclosed in U.S. Pat. No. 3,790,155, disclose a construction where the remotely operated motors are not attached to the translation slide assembly, but are connected to the assembly by conventional means of lead screws for remote operation. While such a construction does indeed place no motor load on the translation slide, the reference does not address or resolve the problem of orthogonal translation in a vertical plane, but merely orthogonal translation in a horizontal plane. Furthermore, maintaining an external drive system a distance away from the translation table does not provide for a compact, simple and inexpensive unit.

Thus, there is need for a simple, reliable, independent and accurate remote-operated means for providing an easily controlled X-Y movement capability in a vertical plane.

BRIEF SUMMARY OF THE INVENTION

The present invention is an X-Y translation slide adapted to provide independent two dimensional translation of an object in a vertical plane without the weight of the driving system of one stage applying a load to the other stage. Two translation stages are mounted to a vertical backing plate in such a manner that neither acts as a load upon the other, yet each is moveable in a different orthogonal direction in the vertical plane independently. The lower translation stage includes a spring-loaded slide moveably mounted thereto to which the translated object is secured. A pushrod is attached to the upper stage and contacts the slide to provide translation of the object in a direction parallel to the vertical plane. One motor is utilized to drive each translation stage of the translation table; each is mounted to the rear side of the backing plate behind the translation stages in such a manner so as to drive the translation slide through a system of gears in both vertical and horizontal orthogonal directions within a vertical plane.

This invention provides accurate two dimensional movement of a translation slide in a vertical plane which movement is readily achieved in a repeatible, reliable and accurate manner without the necessity of considering and calculating the load placed on the lower translation stage resulting from the weight of the motor driving the upper translation stage. A simple and compact unit is thus disclosed to meet the shortcomings of the prior art.

DETAILED DESCRIPTION OF THE PREFERRED EMBODIMENT

Figure 1:
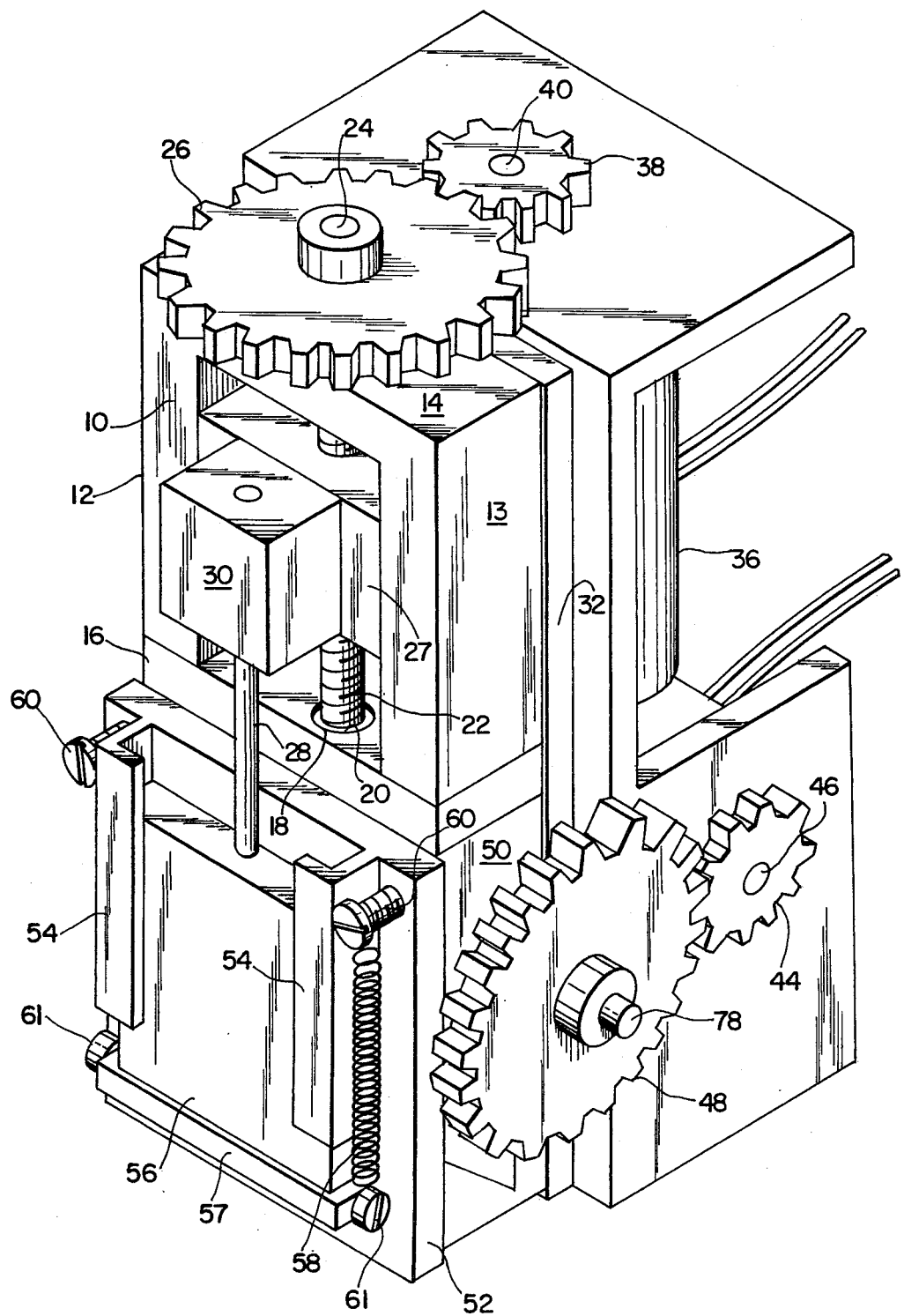
FIG. 1 is a perspective view of the translation slide.

Throughout the three figures illustrating the preferred embodiment of the present invention, like numbers repesent like parts. FIG. 1 illustrates the translation slide wherein a vertical support 10 comprised of two parallel sides 12 and 13 and a perpendicular side 14 is mounted to a vertical support end 16 which is perpendicular to said two parallel sides 12 and 13 of said vertical support 10 such that the structure comprised of said vertical support 10 and said vertical support end 16 comprise a rectangle, preferably a square. Two holes (only one shown) are drilled in the rectangle, hole 18 at the horizontal and lateral midpoint of said vertical support end 16 and the other hole (not shown) at the horizontal and lateral midpoint of the perpendicular side 14 of the vertical support 10 such that the center points of both holes are located in the same vertical plane, but a distance apart.

A ball bearing seal 20 is placed in each hole (only hole 18 is shown) into which seal a vertical screw 22 is mounted. Vertical screw end 24 is of smaller diameter to fit the inner diameter of said seal 20 and is machined to a smooth rod. It extends through the perpendicular side 14 of the vertical support 12 a distance long enough to mount a driven gear 26 thereon. The other end of the vertical screw 22 is machined in a like manner with the machine end fitting within the ball bearing rod 20 in vertical support end 16.

A screw block 27 is mounted on vertical screw 22 in such a manner that vertical screw 22 passes through a like threaded hole tapped through the block at the lateral and vertical midpoint of the screw block 27 such that turning the vertical screw 22 causes the screw block 27 to move vertically on the vertical screw between the perpendicular side 14 of the vertical support 10 and the vertical support end 16. The screw block 27 is such that it is close in length to the width of vertical support 10, yet allows for vertical movement on the vertical screw 22 without binding on the parallel sides 12 and 13 of the vertical support 10. The screw block 27 is of the same thickness as the vertical support 10 but is of width sufficient to allow the desired length of vertical travel of the invention.

A round-tip pushrod 28 is mounted at the vertical and lateral midpoint of a block 30 which is mounted to the screw block 27 by any suitable means, preferably with machine screws, such that the pushrod 28 is parallel to the vertical screw 22. The pushrod 28 is of sufficient length to obtain the desired vertical travel of the translation table slide.

The rectangle comprised of the vertical support 10 and attached vertical support end 16 is mounted flush to a backing plate 32 which in turn is mounted flush to a suitable motor support 34. Motor support 34 may be any suitable structure such that two reversible motors may be permanently mounted upon it in such a manner that the motor support 34 supports the entire weight of each of the motors and that each motor may be mounted in a position whereby a gear mounted to the shaft of each motor directly contacts the gears used to drive the translation stages.

Any suitable motor with its drive shaft 36 is mounted vertically in a suitable manner to the motor supports 34. A drive gear 38 mounted on motor shaft 40 of the motor 36 contacts the driven gear 26 in a suitable manner for driving the vertical screw 22. In a likewise manner, but at a different position on the motor support 34, motor 42 (not shown in FIG. 1) is mounted so that its drive shaft is horizontal such that lateral drive gear 44 mounted on lateral motor shaft 46 contacts the lateral driven screw 76 (shown in FIG. 2) in a suitable manner for driving the gear 48.

A lateral slide assembly 50 is disposed immediately beneath and abutting against the vertical support end 16, being flush mounted to the backing plate 32 in a suitable manner. A plate 52 is mounted to lateral slide assembly 50 by suitable means, as will be more fully described elsewhere.

Two L-shaped slide guides 54 are mounted to or machined as part of the plate 52, being disposed parallel to the direction of travel of the pushrod 28 and each being positioned a preset distance from the edges of the plate 52 parallel to the pushrod 18. A rectangular shaped slide 56 is located between the slide guides 54, to one end of which is attached a slide stop 57. The slide stop 57 is constructed to contact the ends of the slide guides 54 when the slide 56 is at the uppermost vertical point in its travel. The slide 56 is machined on the three surfaces that contact the two slide guides 54 and the backing plate 52. Likewise, the surface contacting the slide 56 is also machined and lightly oiled to reduce the coefficient of friction. The slide 56 is constructed as wide as the distance separating the slide guides 54 will allow, but still allowing it to slide freely within the slide guides 54 and along the backing plate 52. The upper edge of the slide 56 is also machined to reduce the coefficient of friction between the slide 56 and the pushrod 28 where they contact and slide against each other. A spring 58 of strength sufficient to support the load attached to the slide 56 is mounted on one side of a slide guide 54 between the backing plate 52 and the slide stop 57 by screws 60 and 61, respectively. An identical spring (not shown) is mounted in an identical manner on the other side of the front surface of the backing plate 52.

Figure 2:
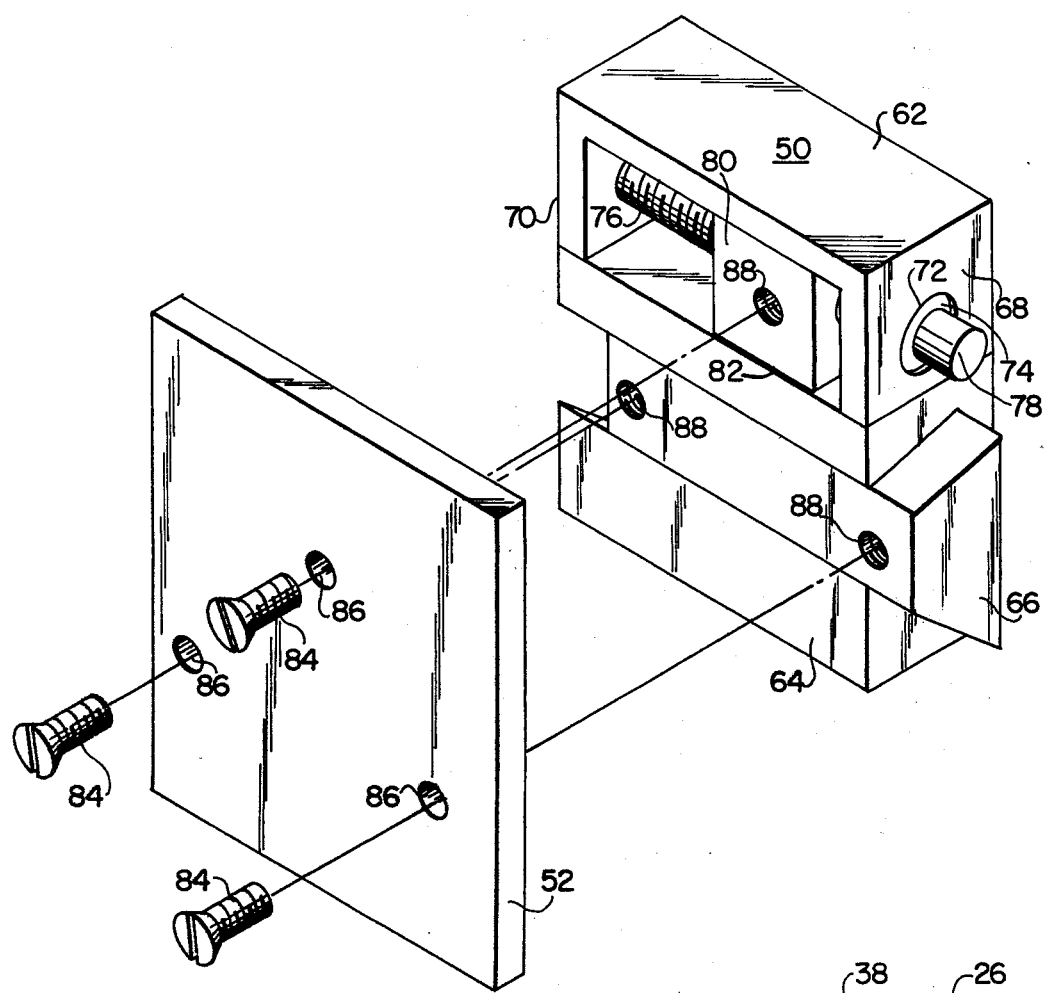
FIG. 2 is a perspective view illustrating the lateral slide assembly of the present invention.

FIG. 2 is a perspective illustration of the lateral slide means 50 which comprises a U-shaped lateral support 62 flush mounted to the side of a suitable slide spport 64 in which a lateral slide 66, preferably of the ball bearing type is mounted. Each of the parallel sides 68 and 70 of the U-shaped lateral support 62 contains a hole 72 (only one of which is shown) positioned in the same place in each parallel side 68 and 70, preferably at the lateral and vertical midpoint of each parallel 68 and 70 side, such that a ball bearing seal 74 is positioned within each hole 68 and 70 and a threaded lateral screw 76 with threads of equal length to the distance between the two seals 74 is mounted there-between with one end having a machined rod-like lateral screw end 78 extending outward from one of the bearings such that lateral driven gear 48 may be mounted thereon in such a manner as to not interfere with the lateral motion of the lateral slide 66. A lateral screw block 80 with a threaded hole (not shown) through its lateral and vertical midsection is mounted on the lateral screw 76 in such a manner and in such a position that when the lateral screw 76 rotates, the lateral screw block 80 moves laterally between the two parallel sides 68 and 70 of the U-shaped lateral support 62. The lateral screw block 80 is of such dimensions as to reduce any wobble encountered when it is moving to minimal levels and a clearance gap 82 is maintained between block 80 and the slide support 64 to reduce the coefficient of friction between the two components. The plate 52, of height and width dimensions approximately equal to those of the lateral assembly 50, is mounted to the lateral slide assembly 50 by three machine screws 84 which pass through three holes 86 drilled in said plate and screw into three holes threaded 88 as shown in said lateral slide 66 and screw block 80 in assembly 50. These three holes 88 are tapped, one in the lateral screw block 80 and the remaining two in the lteral slide 66, such that when the plate 52 is attached, the lateral screw block 80 and the lateral slide 66 are constrained to move together as one unit simultaneously moving plate 52 therewith. The screws 84 are countersunk in the plate 52 to eliminate any potential obstruction with slide 56.

Figure 3:
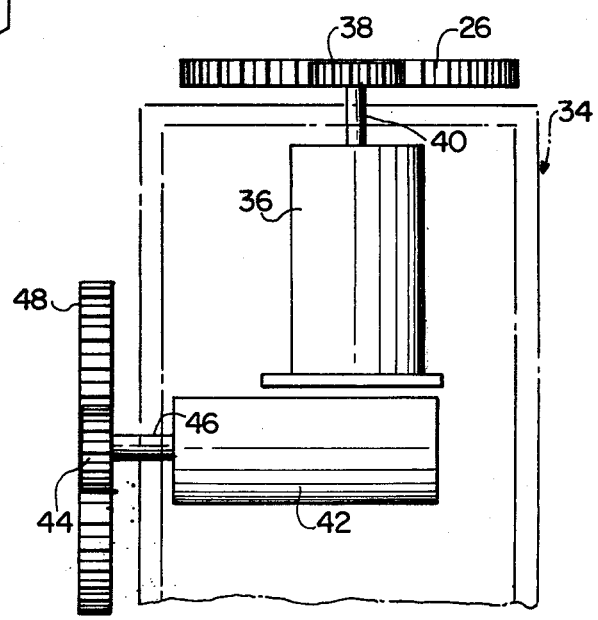
FIG. 3 is a rear view illustrating the placement of the motor drive system of the present invention.

FIG. 3 is a rear view illustration of the back of the motor support 34 and shows the preferred placement of motor 36 and motor 42 thereon. The lateral drive gear 44 is mounted on lateral motor shaft 46 and positioned adjacent in the same plane to and contacting lateral driven gear 48 to provide remote-operated movement in the X-direction of the lateral translation stage. The vertical drive gear 38 is mounted on vertical motor shaft 40 and positioned adjacent in the same plane to and contacting vertical driven gear 26 to provide remote-operated movement in the Y-direction of the vertical translation stage. It should be noted that it is desirable to use small diameter lateral and vertical drive gears 44 and 38 with larger diameter lateral and vertical gears 48 and 26 so that the maximum fine adjustment of the translation stages may be obtained.

In operation, to translate the vertical translation stage, vertical motor 36 is activated to cause vertical motor shaft 40 and vertical drive gear 38 to be rotated. This in turn causes vertical screw 22 to rotate, at a rate slower than the vertical motor shaft 40, and screw block 27 moves along the screw 22 and the pushrod 28 moves against the slide 56 such that said slide is caused to move in a vertical manner; either because of the action of the pushrod 28 on the slide 56, or the spring action of the springs 58.

To translate the lateral translation stage, lateral motor 42 is activated to cause lateral drive gear 44 to rotate on lateral motor shaft 46. This in turn causes lateral screw 76 to rotate, at a slower rate than the lateral motor shaft, and lateral screw block 80 moves along the lateral screw 76 such that it causes the lateral slide 66 and plate 52 to move in a lateral manner. The pushrod 28 is run at the end that contacts slide 56 so that as plate 52 moves laterally, the pushrod 28 slides along the machined end surface of the slide 56 which is secured on plate 52 by slide guides 54 and movable laterally therewith. In summary, in lateral translation, the screw block 27 remains fixed but the smooth rounded tip of pushrod 28 attached to block 30 traverses the upper end of the slide 56. In vertical translation, the tip of the pushrod 28 remains fixed in the lateral direction with respect to the upper end of the slide 56, but drives the slide against the springs 58 and the weight of the object being translated due to vertical movement of block 30.

As is obvious to one skilled in the art to which this invention pertains, a precision ball bearing slide that may preferably comprise the lateral slide may also comprise the vertical slide 56. In addition, it may readily be seen that other motor constructions besides the stepper motors preferably utilized by the present invention, such as DC or servo motors may be used in the construction of the invention.

Other embodiments and modifications of the present invention will readily come to those of ordinary skill in the art having the benefit of the teachings presented in the foregoing description and the drawings. It is, therefore, to be understood that this invention is not to be limited thereto and that said modifications and embodiments are intended to be included within the scope of the appended claims.

What is claimed and desired to be secured by Letters Patent of the United States is:

1. Apparatus for providing two dimensional translation in a vertical plan comprising:
   a first means mounted relative to a backing plate parallel to said vertical plane and adapted for linear motion in a first direction with respect to said plate;
   a second means mounted relative to said backing plate, parallel to said vertical plane, and adapted for linear motion in a second direction substantially orthogonal to said first direction;
   a third means moveably mounted into said second means, and a pushrod means mounted on said first means for providing linear translation to said third means in said first direction in response to said linear movement of said first means;
   a fourth means mounted relative to said backing plate and adapted for rotational motion with respect to said plate;
   a first drive gear means mounted relative to said first means for operationally connecting said first means to said fourth means whereby rotational motion of said fourth means causes movement of said first means in said first direction;
   a first motor drive means for driving said first drive gear means;
   a fifth means mounted relative to said backing plate and adapted for rotational motion with respect to said plate; and a second gear means mounted relative to said second means for mechanically connecting said second means to said fifth means whereby the rotational motion of said fifth means causes translation of said second means in said second directions and
   a second motor drive means for driving said second gear means independent of said first motor drive means.

* * * * *